United States Patent [19]

Kanayama et al.

[11] Patent Number: 6,076,004
[45] Date of Patent: *Jun. 13, 2000

[54] MAGNETIC RESONANCE IMAGE CORRECTION METHOD AND MAGNETIC RESONANCE IMAGING APPARATUS USING THE SAME

[75] Inventors: Shoichi Kanayama, Saitama; Arturo Calderon, Kanagawa, both of Japan

[73] Assignee: Kabushiki Kaisha Toshiba, Kawasaki, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/708,667

[22] Filed: Sep. 5, 1996

[30] Foreign Application Priority Data

Sep. 5, 1995 [JP] Japan .................................. 7-227632

[51] Int. Cl.$^7$ .................................................. A61B 5/055
[52] U.S. Cl. .......................... 600/410; 324/309; 324/312; 128/920; 128/922; 382/278; 382/280; 382/296; 382/298
[58] Field of Search .............................. 128/653.2, 653.3, 128/653.4, 920, 922; 324/309, 312; 382/278, 280, 296, 298, 128, 130, 131

[56] References Cited

U.S. PATENT DOCUMENTS

| | | | |
|---|---|---|---|
| 4,084,255 | 4/1978 | Casasent et al. | 364/822 |
| 5,565,777 | 10/1996 | Kanayama et al. | 324/309 |

FOREIGN PATENT DOCUMENTS

| | | |
|---|---|---|
| 7-79943 | 3/1995 | Japan . |

OTHER PUBLICATIONS

S. Ogawa et al., "Oxygenation–Sensitive Contrast in Magnetic Resonance Image of Rodent Brain at High Magnetic Fields", Magnetic Resonance in Medicine, vol. 14, 1990, pp. 68–78.

J. A. Detre et al., "Perfusion Imaging", Magnetic Resonance in Medicine, vol. 23, 1992, pp. 37–45.

R. T. Constable et al., "Functional Brain Imaging at 1.5 T Using Conventional Gradient Echo MR Imaging Techniques", Magnetic Resonance Imaging, vol. 11, pp. 451–459, 1993.

Q. Chen et al., "Symmetric Phase–Only Matched Filtering of Fourier–Mellin Transforms for Image Registration and Recognition", IEEE Transactions on Pattern Analysis and Machine Intelligence. Vol. 16, No. 12, Dec. 1994.

A. Kassam et al., "3D Registration of fMRI Brain Images Based on K–space information", Proc. of the Soc. of Mag. Resonance, 3rd Scientific Meeting, pp. 236, 1995.

R. M. Weisskoff et al., "MRI Susceptometry: Image–Based Measurement of Absolute Susceptibility of MR. Contrast Agents and Human Blood", Magnetic Resonance in Medicine, vol. 24, pp. 375–383 (1992).

K. K. Kwong et al., "Dynamic Magnetic Resonance Imaging of Human Brain Activity during Primary Sensory Stimulation", Proc. Natl. Acad. Sci., vol. 89, pp. 5675–5679, Jun. 1992.

B. P. Poncelet, et al., "Brain Parenchyma Motion: Measurement with Cine Echo–Planar MR Imaging", Neuroradiology, 1992, vol. 185, pp. 645–651.

*Primary Examiner*—Ruth S. Smith
*Attorney, Agent, or Firm*—Foley & Lardner

[57] ABSTRACT

Cross-correlation between a first magnetic resonance image as a reference image and a second magnetic resonance image to be adjusted relative to the first magnetic resonance image is taken, deviation of the second magnetic resonance image to the first magnetic resonance image as correction values is calculated, and the second magnetic resonance image based on the correction values is corrected.

14 Claims, 5 Drawing Sheets

MAGNETIC RESONANCE IMAGE CORRECTION METHOD AND MAGNETIC RESONANCE IMAGING APPARATUS USING THE SAME

BACKGROUND OF THE INVENTION

1. Field of the Invention

The present invention relates to a magnetic resonance imaging apparatus which applies a radiofrequency magnetic field and a gradient magnetic field to a body placed in an uniform magnetostatic field according to a predetermined pulse sequence, and detects the magnetic resonance signal from the body to be tested to image the internal information of the body to be tested as a magnetic resonance image, and a magnetic resonance image correction system used for the apparatus.

2. Description of the Related Art

The magnetic resonance imaging method is, as well known, a method to form an image of the chemical and physical microscopic properties of materials, by utilizing a phenomenon which resonantly absorbs the energy in the radiofrequency magnetic field which rotates at a specific frequency, when a group of nuclear spins having an inherent magnetic moment is located in an uniform magnetostatic field.

In this magnetic resonance imaging method, there can be obtained images having various contrasts, such as an image with a contrast in which a longitudinal relaxation time $T_1$ of the nuclear spin is emphasized (hereinafter referred to as "$T_1$ image"), an image with a contrast in which a transverse relaxation time $T_2$ of the nuclear spin is emphasized (hereinafter referred to as "$T_2$ image"), an image with a contrast in which the density distribution of the nuclear spin is emphasized (hereinafter referred to as "density image"), an image with a contrast in which a transverse relaxation time $T_2$ of the nuclear spin and an actual transverse relaxation time $T_2^*$ reflecting an abrupt phase change of the nuclear spin due to the microscopic nonuniformity of the magnetic field in the voxel are emphasized (hereinafter referred to as "$T_2^*$ image"), and the like.

As described in "Perfusion Imaging" (John A. Detre et al., Magnetic Resonance in Medicine, 23, pp.37–45 (1992)), when an amount of local bloodstream or a flow rate of bloodstream in the living body tissue changes, in certain imaging methods of the magnetic resonance imaging apparatus, it is observed that the relaxation time (for example, $T_1$ and the like) of the living body tissues apparently changes, and the image contrast is changed. In these imaging methods, information relating to the perfusion and diffusion in the living body can be effectively obtained by utilizing a contrast medium. In the imaging method with regard to perfusion and diffusion, there are often determined the difference among a plurality of images in order to examine the timewise change, or the adding average in order to detect minute signal change. In this case, however, there is a problem of positional deviation among images due to the movement of a living body and the like.

On the other hand, as described in "Oxygenation-Sensitive Contrast in Magnetic Resonance Image of Rodent Brain at High Magnetic Fields". (Seiji Ogawa et al., Magnetic Resonance in Medicine, 14, pp.68–78 (1990)), it is known that among hemoglobins in the blood in the living body, oxidized hemoglobin contained in a large amount in the arterial blood shows the diamagnetism, and reduced hemoglobin contained in a large amount in the venous blood shows the paramagnetism. And as described in "MRI Susceptometry: Image-Based Measurement of Absolute Susceptibility of MR Contrast Agents and Human Blood", (Robert M. Weiskoff and Suzanne Kiihne, Magnetic Resonance in Medicine, 24, pp.375–383 (1992)), the oxidized hemoglobin which is a diamagnetic substance hardly disturbs local magnetic fields (the difference in the magnetization rate from that of the living body tissue: 0.02 ppm), but the reduced hemoglobin which is a paramagnetic substance has a large difference in the magnetization rate from that of the peripheral tissues (the difference in the magnetization rate from that of the living body tissue.: 0.15 ppm) and locally disturbs the magnetic field, thereby $T_2^*$ is shortened.

By utilizing tile above-mentioned property, changes in the oxygen density and changes in the bloodstream due to the physiological functions, such as activation of cells in the living body tissues, for example, activation of the visual cortex in the cerebral cortex with the stimuli of light can be imaged, which is described in "Dynamic magnetic resonance imaging of human brain activity during primary sensory stimulation", (Kenneth K. Kwong et al., Proc. Natl. Acad. Sci. USA 69, pp.5675–5679 (June 1992) Neurobiology) and the like. As the image-sensing method used in forming their image, there is a method based on a pulse sequence, generally called as a gradient echo method and an echo planar method.

However, the signal change (change in the image contrast) caused due to the physiological functions in the living body obtained by these imaging methods is very small. Therefore, as a method for detecting this small signal change, there have been conventionally used a method to take the difference of images before and after the phenomenon of the physiological functions or a method to carry out the statistical processing. As the statistical data-processing method, there can be mentioned a method using the paired-samplet-test detection method which is described in "Functional Brain Imaging at 1.5T using Conventional Gradient Echo MR Imaging Techniques", (R. T. Constable et al., Magnetic Resonance Imaging, Vol. II. pp.451–459, 1993) or the like. Here, when the statistical processing is carried out, since a plurality of images are required, the time for taking images becomes long. On the other hand, when image subtraction is used, it is necessary to obtain an image with high S/N ratio. Accordingly, both methods are readily affected by the movement of a living body.

As a method to correct the movement of the living body, there is a method to correct the scale and the position of the image per se, i.e., to perform a pattern matching. As a well-known method in this pattern matching, there is a method to utilize the cross-correlation among images. The example in which the magnetic resonance image is corrected by utilizing the cross-correlation of phases is described in "Symmetric Phase-Only Matched Filtering of Fourier-Mellin Transforms for Image Registration and Recognitions, (Qin-sheng Chen et al,, IEEE TRANSACTIONS ON PATTERN ANALYSIS AND MACHINE INTELLIGENCE, VOL. 16 NO.12 pp.1156–1168 (1994)).

Furthermore, though it is well known that a distortion in images is caused when the distribution of the magnetostatic field is not uniform, the distortion in images is particularly conspicuous in the imaging method with the $T_2^*$ contrast which is used for the detection of the Phenomenon of physiological functions, such as the cell activation of the living body described above. The method to correct such distortions in images by using the affine transformation is described in Japanese Patent Application Laid-open No. 7-79943.

When data are processed between a plurality of images in order to form an image of informations of the perfusion, diffusion, cell activation and the like in the living body, If there is any inconsistency of images caused by the deviation in position or the change in scale of images due to the influences of movements of a living body, it is difficult to clearly form the image of informations of perfusion, diffusion, cell activation and the like.

It is well known that the scale and the position of the brain actually change simultaneously with the heartbeat, as described in "Brain Parenchyma Motion: Measurement with Cine Echo-Planar MR Imaging", (Brigitte P. Poncelet et al., Radiology, 185, pp.645–651 (1992)).

As described above, in the conventional method, there has been a problem that various physiological functional informations in the living body cannot be detected correctly due to the influences of movements of the body accompanied with the respiration, heartbeat and the like.

SUMMARY OF THE INVENTION

The present invention has been completed under this background. The object of the present invention, therefore, is to provide a magnetic resonance image correction system and a magnetic resonance imaging apparatus utilizing the system which can adjust the deviation among magnetic resonance images to obtain the physiological functional informations in the body to be tested at high accuracy.

In order to attain the above objects, there is provided a magnetic resonance image correction method comprising: taking cross-correlation between d first magnetic resonance image as a reference image and a second magnetic resonance image adjusted to the first magnetic resonance image, calculating deviation of the second magnetic resonance image to the first magnetic resonance image as correction values, and correcting the second magnetic resonance image based on the correction values.

According to the present invention, the physiological functional information in the body to be tested can be obtained at high accuracy.

In the preferred aspect of the present invention, the first magnetic resonance image and the second magnetic resonance image are respectively subjected to the fast Fourier transform, and the deviation relating to scale and rotation is corrected, thereafter the deviation relating to position is independently corrected.

According to this aspect, deviation relating to scale and rotation an: deviation relating to position can be independently corrected.

In the preferred aspect of the present invention, the correction values are determined as the coefficients which make the cross-correlation function become maximum.

In the preferred aspect of the present invention, the first magnetic resonance image and the second magnetic resonance image subjected to the fast Fourier transform are transformed to polar coordinates, respectively, then deviations relating to scale and rotation are corrected.

In the preferred aspect of the present invention, coordinate scales in each respective radial direction of the first magnetic resonance image and the second magnetic resonance image transformed to polar coordinates are transformed logarithmically, then deviations relating to scale and rotation are corrected.

In the preferred aspect of the present invention, deviations relating to the position are corrected in the form of orthogonal coordinates.

In the preferred aspect of the present invention, the cross-correlation may be a cross-correlation relating to phase.

In the preferred aspect of the present invention, the cross-correlation may be a cross-correlation relating to amplitude.

In the preferred aspect of the present invention, the cross-correlation may be a cross-correlation relating to phase and amplitude.

In the preferred aspect of the present invention, processing relating to the correction is repeated plural times until the deviation becomes a predetermined allowable value.

In order to attain the above-mentioned object, there is provided a magnetic resonance imaging apparatus comprising: a magnetostatic field-forming magnet for forming a uniform magnetostatic field to a body to be tested; a gradient magnetic field-forming coil for applying a gradient magnetic field to the body to be tested; means for applying a radiofrequency magnetic field to the body to be tested; means for receiving a magnetic resonance signal from the body to be tested obtained according to the application of the radiofrequency magnetic field; means for forming an image of the magnetic resonance signal; a magnetic resonance image correction means for taking cross-correlation between a first magnetic resonance image as a reference image and a second magnetic resonance image obtained by the image-forming means, calculating deviation of the second magnetic resonance image relative to the first magnetic resonance image as correction values, and correcting the second magnetic resonance image based on the correction values; and means for displaying the second magnetic resonance image corrected by the magnetic resonance image correction means.

In the preferred aspect of the present invention, the magnetic resonance image correction means comprises: a scale/rotation correction means for subjecting the first magnetic resonance image and the second magnetic resonance image to fast Fourier transform, respectively, and correcting the deviation relating scale and rotation; and a position correction means for correcting the deviation relating to position independently.

In the preferred aspect of the present invention, image the first magnetic resonance image as the reference may be a first image among a series of magnetic resonance images obtained by the image-forming means.

In the preferred aspect of the present invention, the first magnetic resonance image used as the reference may be an image selected via a console terminal by an operator, among a series of magnetic resonance images obtained by the image-forming means.

In the preferred aspect of the present invention, a magnetic resonance imaging apparatus further comprises a stimulus device for giving stimuli to the body to be tested.

In the preferred aspect of the present invention, the second magnetic resonance image is an image obtained while stimuli are given to the body to be tested by the stimulus device.

The nature, principle and utility of the invention will become more apparent from the following detailed description when read in conjunction with the accompanying drawings.

DESCRIPTION OF THE PREFERRED EMBODIMENTS

Now, the embodiments of the present invention will be described in detail with reference to the accompanying drawings.

Figure 1:
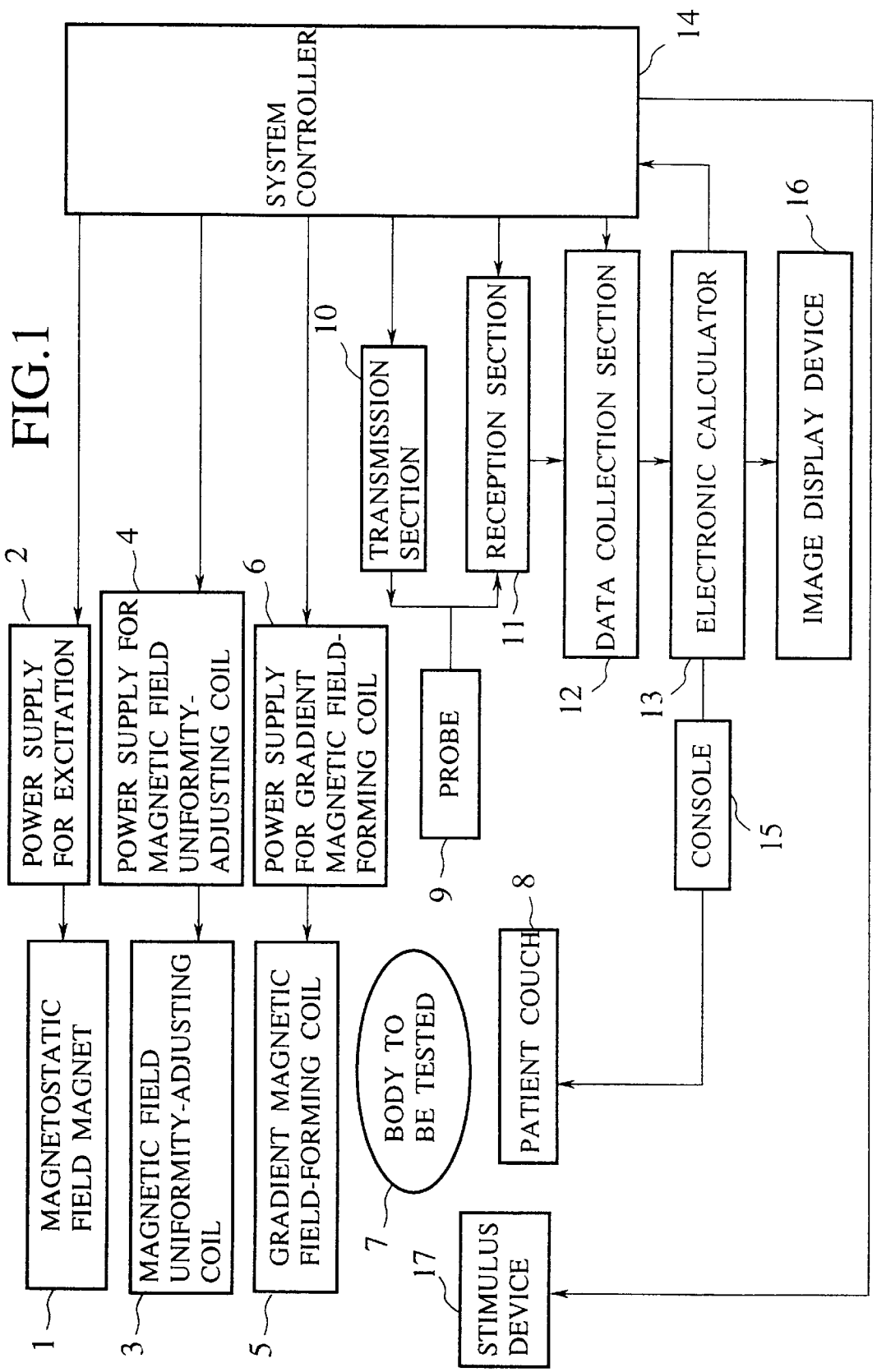
FIG. 1 is a block diagram showing the structure of one embodiment in the magnetic resonance imaging apparatus of the present invention.

FIG. 1 is a block diagram showing the structure of one embodiment ia the magnetic resonance imaging apparatus of the present invention. In FIG. 1, magnetostatic field magnet 1, magnetic field uniformity-adjusting coil 3, and gradient magnetic field-forming coil 5 are driven, respectively, by a power supply for the excitation 2, a power supply for the magnetic field uniformity-adjusting coil 4, and a power supply for the gradient magnetic field-forming coil 6, respectively. By the magnetostatic field magnet 1 and the magnetic field uniformity-adjusting coil 3, uniform magnetostatic field is applied to the body to be tested 7. The gradient magnetic field produced by the gradient magnetic field-forming coil 5, which has the three-directional linear gradient magnetic field distribution orthogonal to each other, is applied in the same direction with the magnetostatic field. In order to apply the radiofrequency magnetic field to the body to be tested 7, a radiofrequency signal is sent from the transmission section 10 to the probe 9. Furthermore, the magnetic resonance signal from the body to be tested 7 in response to this radiofrequency magnetic field is received by the probe 9. Here, probe 9 may be for both transmission and reception, or may be provided separately for transmission and for reception. The magnetic resonance signal received by probe 9 is transferred to the data collection section 12, after the quadrature phase thereof is detected at the reception section 11, and A/D converted. The magnetic resonance signal A/D converted at the data collection section 12 is transferred to the electronic calculator 13. All the power supply for excitation 2, the power supply for magnetic field uniformity-adjusting coil 4, the power supply for gradient magnetic field-forming coil 6, the transmission section 10, the reception section 11, and the data collection section 12 are controlled by the system controller 14. The system controller 14 is controlled by the console 15 via the electronic calculator 13.

The electronic calculator 13 reconstructs the magnetic resonance image based on the magnetic resonance signal sent from the data collection section 12 to obtain the magnetic resonance image data. The obtained magnetic resonance image date is displayed on the image display device 16. The electronic calculator 13 and the bed 8 are controlled by the console 15.

The pulse sequence for collecting the magnetic resonance image data from a slice in the body to be tested 7 and the stimulus device 17 which gives stimuli such as light, sound and the like to the body to be tested 7 in the present embodiment are controlled by the system controller 14.

Figure 2:
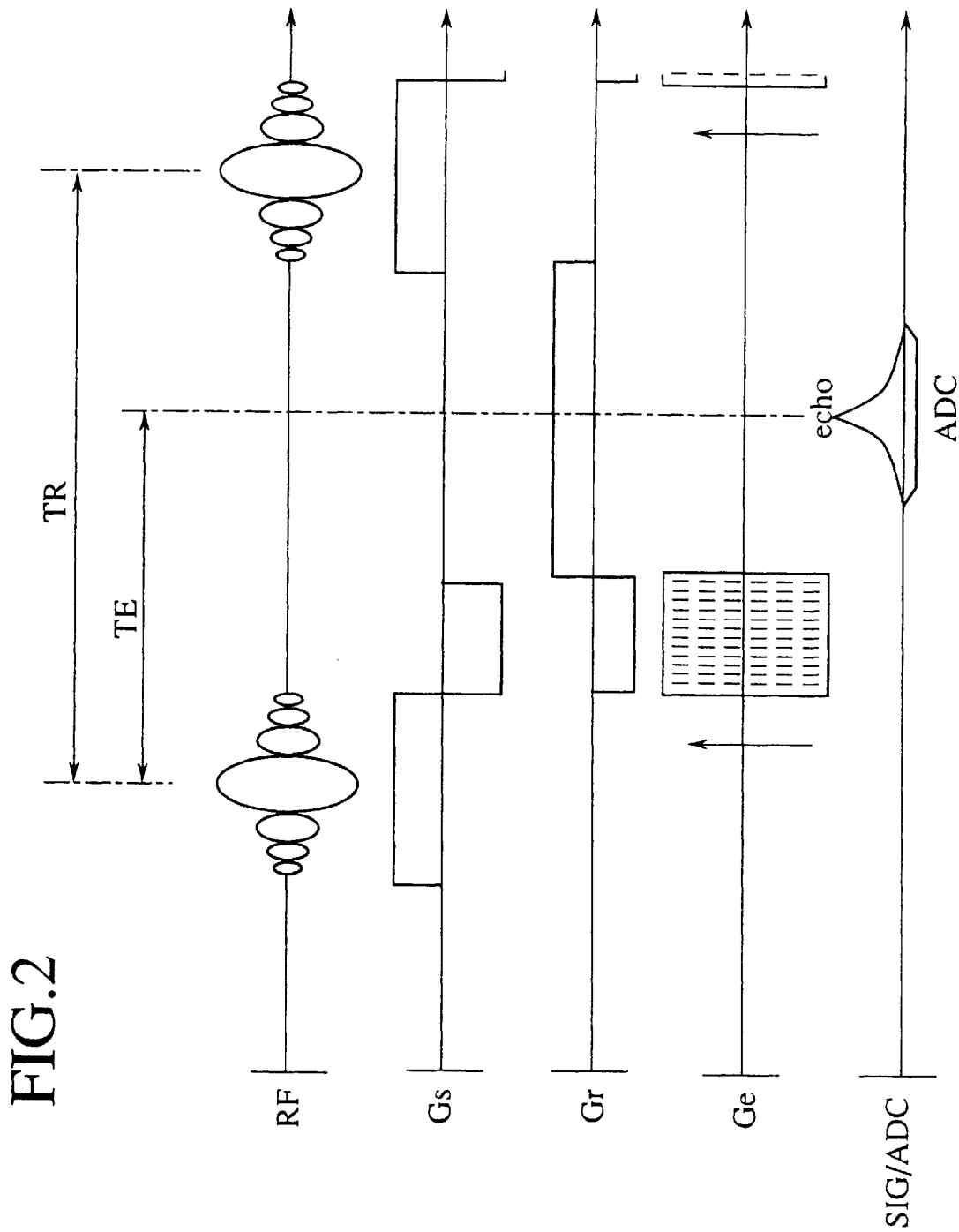
FIG. 2 is a view for illustrating the pulse sequence by the field echo method for forming a physiological functional image in the body to be tested.
Figure 3:
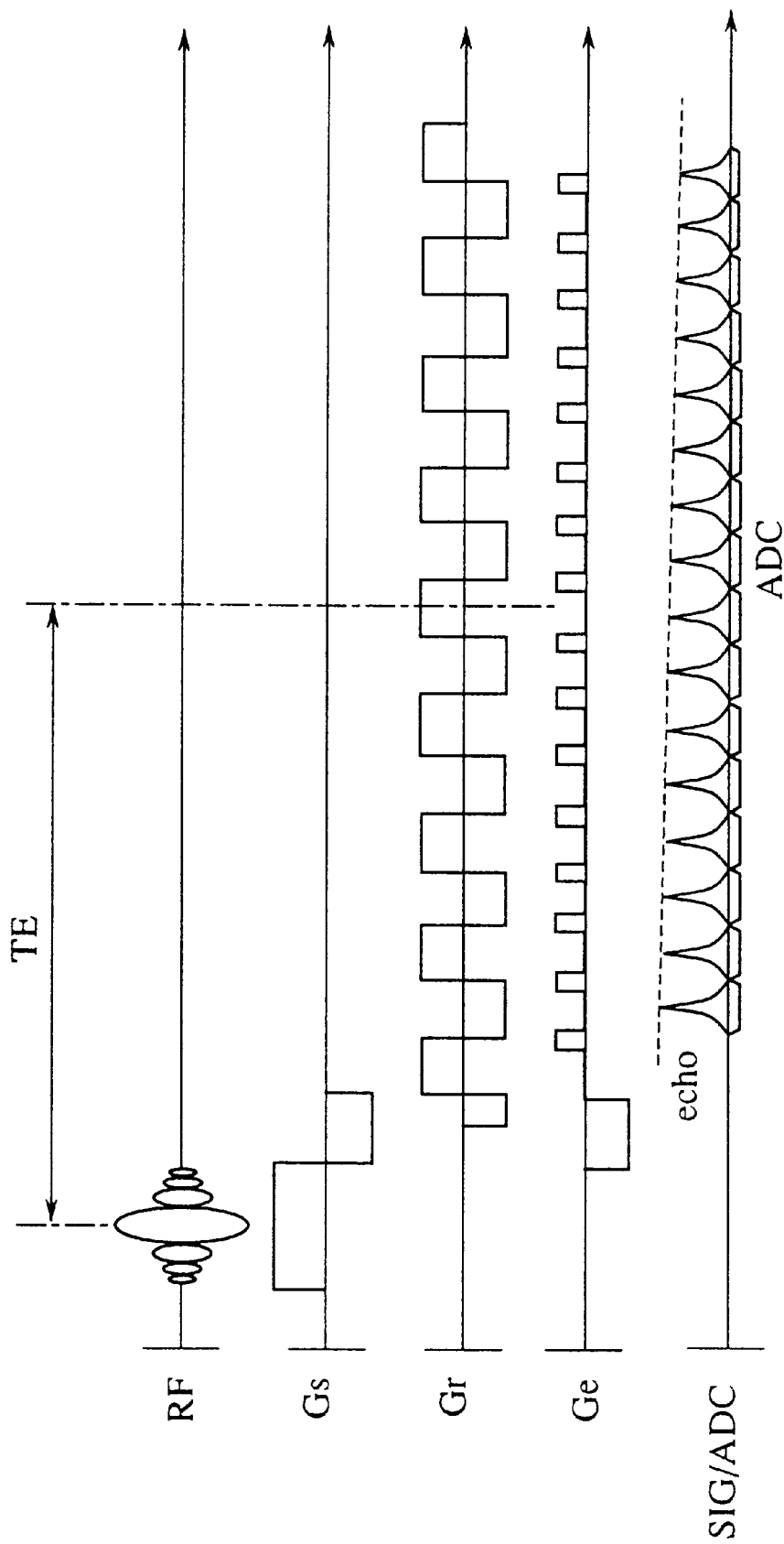
FIG. 3 is a view for illustrating the pulse sequence by the echo planar method for forming a physiological functional image in the body to be tested.

FIG. 2 and FIG. 3 are views for illustrating the pulse sequence by means of the field echo method and the pulse sequence by means of the echo planar method. respectively, for forming the physiological functional image in the body to be tested 7 according to the present embodiment. In the drawing, RF is the radiofrequency magnetic field, Gs, Gr and Ge are the gradient magnetic fields, respectively, for slice, for reading out, and for phase encoding. Furthermore, SIG/ADC shows, respectively, the timing for the magnetic resonance signal and the timing for the data collection (sampling). Here, Gs is the gradient magnetic field for slice to excite the desired region in the body to be tested 7, Gr is the gradient magnetic field for reading out to encode the positional information into the frequency information of the magnetic resonance signal, and Ge is the gradient magnetic field for phase encoding to encode the positional information into the phase information of the magnetic resonance signal.

Referring to FIG. 2, the radiofrequency magnetic field pulse RY and the gradient magnetic field for slice Gs are first applied to excite selectively the magnetization spin in the desired region, and the automatic inductive attenuated NMR signal is generated. Then, the gradient magnetic field for phase encoding Ge and the gradient magnetic field for reading out Gr are sequentially applied to collect the echo signal "echo" generated during the application of the gradient magnetic field for reading out Gr. Similar pulse sequence is repeated for the repetition time TR, the amount to be applied of the gradient magnetic field for phase encoding Ge being sequentially changed. In the case of this method, the typical conditions for forming physiological functional images are as follows: the repetition time TR is from 50 to 100 mm/sec., and the echo time TE (time interval from the center of the radiofrequency pulse RF to the data which becomes the center when data are arranged) is from 30 to 70 mm/sec. Furthermore, the excitation angle (flip angle) of the spin by means of the radiofrequency magnetic field pulse is from 10 to 40 degrees.

Referring to FIG. 3, the radiofrequency magnetic field pulse RF and the gradient magnetic field Gs are first applied to excite selectively the magnetization spin in the desired region, and the automatic inductive attenuated NMR signal is generated. Then, a plurality of echo signals are sequentially generated, while the gradient magnetic field for reading out Gr is switched alternately to positive and negative (polarity inversion), and the gradient magnetic field for phase encoding Ge is applied to every echo signal, respectively. A plurality of echo signals "echo" generated, respectively, in the vicinity of the center of the gradient magnetic field for reading out Gr are collected. In this case, one spin excitation can obtain the data for one image. In the case of this method, the typical conditions for forming physiological functional images are as follows: the echo time TE (time interval from the center of the radiofrequency pulse RF to the data which becomes the origin when data are arranged two-dimensionally) is from 50 to 70 mra/sec.

The pulse sequences of FIG. 2 and FIG. 3 are repeated and subjected to proper pre-processing and then are subjected to complex Fourier transform, thereby a series of magnetic resonance image groups which continue in time series are collected. Thus obtained magnetic resonance images are images with $T_2^*$ contrast, and as described above, react to stimuli and load so that a particular portion of the brain cells is activated, and can detect the change in $T_2^*$ contrast according to the change in magnetization rate in the activated portion and the vicinity thereof, caused by the change of oxygen concentration in the tissue and the change of the local bloodstream. Furthermore, depending on the above-mentioned conditions of the pulse sequence, it can also catch the contrast change according to the bloodstream change per se in response to the stimuli and load.

Actually, in order to obtain physiological functional information by using the aforementioned pulse sequence, it is necessary to perform the image processing, such as averaging, difference, and statistic processing for magnetic resonance images of a plurality of frames when the stimuli and load are imparted and when they are not imparted, that is, magnetic resonance images of at least two frames collected at a time before and after the stimuli are imparted. Therefore, in order to obtain physiological functional informations at high accuracy, it is necessary to adjust the deviations (position, rotation, and scale) among these magnetic resonance images. The image processings required for adjusting the deviations among a series of plural magnetic resonance images according to the present invention are performed in the electronic calculator 13 at a pre-stage of image processings of, for example, averaging, difference and statistic processings.

Now, the image processing for adjusting the deviations among a plurality of magnetic resonance images will be described.

Figure 4:
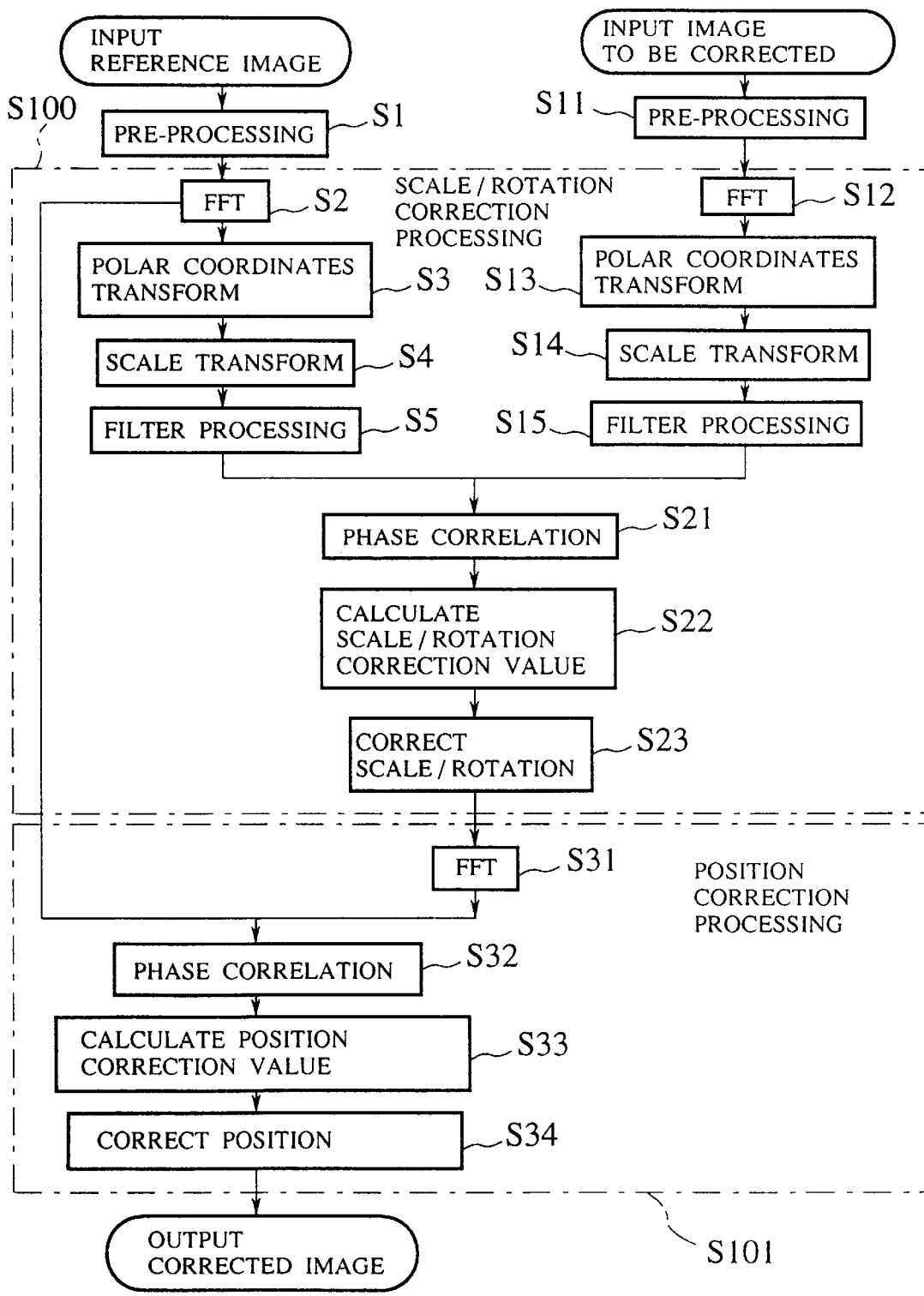
FIG. 4 is a flow chart showing the procedure of image processing required to adjust deviations among a plurality of magnetic resonance images.

FIG. 4 is a view showing the procedure of image processing required for adjusting deviations among a plurality of magnetic resonance images.

First, the reference image data (the first magnetic resonance image data) which is to be a reference and the image data (the second magnetic resonance image data) to for which the deviation is to be adjusted to the reference image are input. The reference image, may be selected among a series of magnetic resonance image groups by an operator via a console 15, or the magnetic resonance image imaged first, among a series of magnetic resonance image groups, may be selected as the reference image. As the magnetic resonance image, two-dimensional image data or three-dimensional image data may be used. Here, the description will be made for the two-dimensional image data. In the present embodiment, the reference image data is expressed as RE(x, y), and the image data to be corrected is expressed as F(x, y).

First, the reference image data and the image data to be corrected are subjected to pre-processings such as interpolation processing, filter processing and mask processing, as required (Step 1, Step 11). Thereafter, the scale/rotation correction processing is performed (Step 100), and the position correction processing is further performed (Step 101).

The scale/rotation correction processing will now be described in detail. First, the reference image data RE(x, y) and the image data to be corrected F(x, y) are subjected to FFT (fast Fourier transform), respectively, to obtain the corresponding space frequency data re(kx, ky), f(kx, ky) (Step 2, Step 12).

Then, the respective absolute values of the space frequency data re(kx, ky) and f(kx, ky) are transformed to the data in the form of polar coordinates, |re'(kr, θ)|, |f'(kr, θ)|, so as to make it easy to handle the rotation of the image (Step 3, Step 13). Furthermore, the coordinate scale of the data in the form of polar coordinates, |re'(kr, θ)|, |f'(kr, θ)| in the radial direction are logarithmically transformed to the data in the form of polar coordinates, |re"(ln(kr), θ)|, |f"(ln(kr), θ)|, so as to make it easy to handle the scale of the image (Step 4, Step 14). Incidentally, ln(kr) represents the scale of image with respect to the original image, and θ represents the rotation.

Data |re"(ln(kr), θ)|, |f"(ln(kr), θ)| are subjected to a proper filter processing such as Hamming filtering to obtain the data |re^(ln(kr), θ)|, |f^(ln(kr), θ)| (Step 5, Step 15).

Between both image data |re^(ln(kr), θ)|, |f^(ln(kr), θ)| which have been subjected to filter processing, the cross-correlation of phase Is calculated (Step 21). That is, the function pc1(ln(kr), θ) is determined based on Equation (1), wherein * shows the complex conjugate.

$$pc1(\ln(kr), \theta) = \frac{r^\wedge(\ln(kr), \theta) \cdot f^{\wedge *}(\ln(kr), \theta)}{|r^\wedge(\ln(kr), \theta) \cdot f^{\wedge *}(\ln(kr), \theta)|} \quad (1)$$

Next, the function pc1(ln(kr), θ) is subjected to IFFT (inverse fast Fourier transform) to obtain the cross-correlation function PC1(ln(r), θ) of the phase between both images.

ln(r) and θ are determined as the correction value with regard to the scale and the rotation, respectively, so that the value of this cross-correlation function PC1(ln(r), θ) becomes maximum. This correction value is assumed to be $\lambda_{PC}$ and $\theta_{PC}$, respectively. Provided that, $\lambda_{PC}$ is a scale factor in the frequency space, and is required to be transformed to the scale factor in the actual space in order to perform the correction processing of the image in the actual space, and concretely, $1/\lambda_{PC}$ is assumed to be the scale factor in the actual space.

As the last step of the scale/rotation correction processing (Step 100), the correction is actually made to the image to be corrected, with respect to the scale and the rotation by using Equations (2), (3) and (4).

$$F^\sim(x,y)=F(x',y') \quad (2)$$

$$x'=1/\lambda_{pc}\{x \cos(\theta_{pc})+y \sin(\theta_{pc})\} \quad (3)$$

$$y'=1/\lambda_{pc}\{-x \sin(\theta_{pc})+y \cos(\theta_{pc})\} \quad (4)$$

Now, the position correction processing (Step 101) will be described. First, the above-mentioned scale/rotation correction image data F~(x, y) is subjected to FFT to obtain the space frequency data f~(kx, ky) (Step 31). Between the space frequency data f~(kx, ky) and the space frequency data r(kx, ky) of the reference image, the cross-correlation of the phase is calculated (Step 32). Namely, the function pc2(kx, ky) is determined based on Equation (5).

$$pc2(kx, ky) = \frac{r(kx, ky) \cdot f^{\sim *}(kx, ky)}{|r(kx, ky) \cdot f^{\sim *}(kx, ky)|} \quad (5)$$

Then, the function pc2(kx, ky) is subjected to IFFT (inverse fast Fourier transform) to obtain the cross-correlation function PC2(x, y) of the phase between both images.

As the correction value of position, x and y are determined so that the value of this cross-correlation function PC2(x, y) becomes maximum (Step 33). This correction value is assumed to be $X_{PC}$ and $Y_{PC}$.

As the last step of position correction processing (Step 101), the correction is actually made to the image to be corrected, with respect to the position by using Equation (6) (Step 34). In addition, thereafter, interpolation processing and filter processing may be performed as required.

Thus, the corrected image $F_{OUT}$ in which the scale. rotation and position are adjusted to the reference image can be obtained.

$$F_{OUT}(x, y)=F^\sim(x-x_{pc}, y-y_{pc}) \quad (6)$$

Incidentally, in the above description, the cross-correlation of only the phase of the space frequency data of the magnetic resonance image has been utilized, but it may be the general cross-correlation using both amplitude and phase or the cross-correlation using only the amplitude. The cross-correlation function utilizing both is determined by utilizing only the numerator in Equation (1) or Equation (5), designating 1(one) to the denominator. The cross-correlation function utilizing only the amplitude is determined by utilizing only the denominator in Equation (1) or Equation (5).

Figure 5:
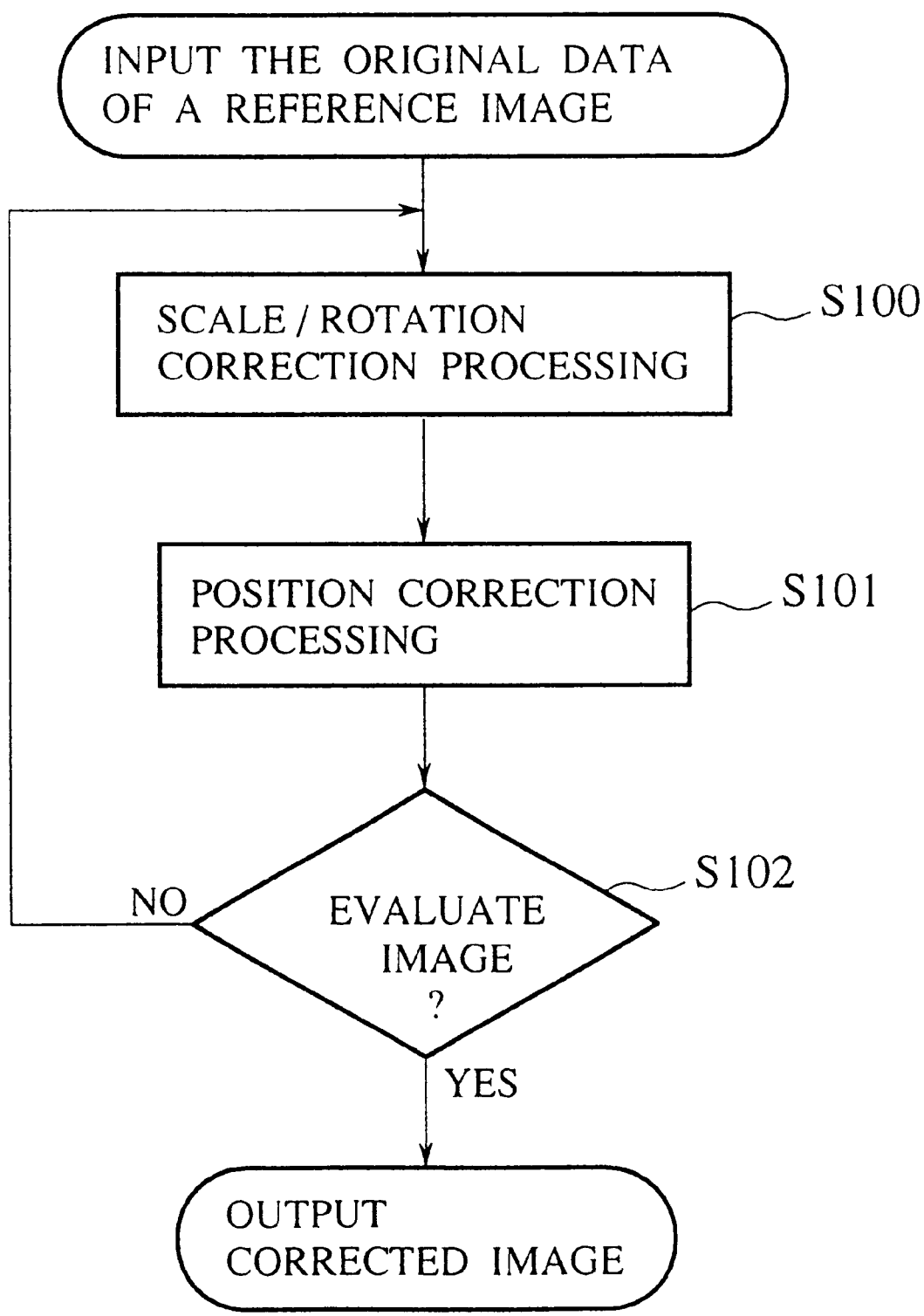
FIG. 5 is a flow chart showing the processing procedure when the scale/rotation processing and the position correction processing are carried out in plural times.

Furthermore, as shown in FIG. 5, a sufficiently corrected image cannot be obtained by scale/rotation correction processing (Step 100) and position correction processing S101, of one time, respectively, these processings may be repeated, designating the corrected image $F_{out}1$ (x, y) of the first time as the image to be corrected, and the correction processings (S100, S101) shown in FIG. 4 may be repeated until the desired corrected image can be obtained.

The present invention can perform processings by changing the form variously other than described above, so far as the scope of the invention is not impaired. For example, in the above description, the input data is designated as the image data, but it is possible to utilize the original collected data of the image (data developed in k-space). In that case, a part of the processing of FFT and the like may be omitted. Furthermore, in the above description, correction regarding the two-dimensional image data has been shown, but similar correction is possible with respect to the three-dimensional data. In the case of the three-dimensional data, correction parameters with regard to rotation and position are added by 1(one), respectively.

Furthermore, while the present invention to performs the above-mentioned series of processings, it is possible to apply the present invention by changing the form variously, for example, performing only a part of the above-mentioned processings.

Furthermore, the present invention can be applied to not only the perfusion image and the diffusion image but also various magnetic resonance images, other than the above-mentioned embodiment.

In addition, the portions of the scale/rotation correction processing and the position correction processing in the present invention can be supplied in software.

As described above, according to the embodiment of the present invention, the deviations among the magnetic resonance images car be adjusted and the physiological functional information in the body to be tested can be obtained at high accuracy. Particularly, by performing the processing after the fast Fourier transform, the deviation relating to the scale and rotation and the deviation relating to the position can be separately corrected.

What is claimed is:

1. A method for magnetic resonance image correction comprising the steps of:
   subjecting a reference magnetic resonance $T_2$ image and a second magnetic resonance $T_2^*$ image to a fast Fourier transform;
   calculating a cross-correlation between the reference magnetic resonance $T_2^*$ image and the second magnetic resonance $T_2^*$ image,
   calculating scale and rotation correction values for the second magnetic resonance $T_2^*$ image comprising scale and rotation deviation values of said second magnetic resonance $T_2^*$ image relative to said reference magnetic resonance $T_2^*$ image,
   correcting said second magnetic resonance $T_2^*$ image using the scale and rotation correction values to produce a scale/rotation-corrected second magnetic resonance $T_2^*$ image,
   subjecting the scale/rotation-corrected second magnetic resonance $T_2^*$ image to a fast Fourier transform,
   calculating a cross-correlation between the reference magnetic resonance $T_2^*$ image and the scale/rotation-corrected second magnetic resonance $T_2^*$ image,
   calculating a position correction value for the scale/rotation-corrected second magnetic resonance $T_2^*$ image comprising a position deviation value of the scale/rotation-corrected second magnetic resonance $T_2^*$ image relative to the reference magnetic resonance $T_2^*$ image, and
   correcting the scale/rotation-corrected second magnetic resonance $T_2^*$ image using the position correction value to produce a position-corrected second magnetic resonance $T_2^*$ image.

2. A magnetic resonance image correction method according to claim 1, wherein said scale, rotation and position correction values are coefficients that maximize the cross-correlation function.

3. A magnetic resonance image correction method according to claim 1, wherein said reference magnetic resonance $T_2^*$ image and said second magnetic resonance $T_2^*$ image subjected to the fast Fourier transform are transformed to polar coordinates prior to correction of deviations relating to scale and rotation.

4. A magnetic resonance image correction method according to claim 3, wherein coordinate scales in each respective radial direction of said reference magnetic resonance $T_2^*$ image and said second magnetic resonance $T_2^*$ image transformed to the polar coordinates are transformed logarithmically prior to correction of deviations relating to scale and rotation.

5. A magnetic resonance image correction method according to claim 1, wherein correction using the position correction value is performed using orthogonal coordinates.

6. A magnetic resonance image correction method according to claim 1, wherein each cross-correlation is a cross-correlation relating to phase.

7. A magnetic resonance image correction method according to claim 1, wherein each cross-correlation is a cross-correlation relating to amplitude.

8. A magnetic resonance image correction method according to claim 1, wherein each cross-correlation is a cross-correlation relating to phase and amplitude.

9. A magnetic resonance image correction method according to claim 1, further comprising repeating the steps of claim 1 plural times until a desired corrected $T_2^*$ image is obtained.

10. A magnetic resonance imaging apparatus comprising:
    a magnetostatic field-forming magnet for applying a uniform magnetostatic field to a body to be tested;
    a gradient magnetic field-forming coil for applying a gradient magnetic field to said body to be tested;
    means for applying radio frequency magnetic field to said body to be tested;
    means for receiving a plurality of magnetic resonance signals from said body to be tested obtained according to the application of said radio frequency magnetic field;
    means for forming an image from said plurality of magnetic resonance signals;
    means for obtaining a reference magnetic resonance $T_2^*$ image and a second magnetic resonance $T_2^*$ image using said means for forming an image;
    scale/rotation correction means for calculating a cross-correlation between the reference magnetic resonance $T_2^*$ image and the second magnetic resonance $T_2^*$ image, calculating scale and rotation correction values for the second magnetic resonance $T_2^*$ image comprising scale and rotation deviation values of said second magnetic resonance $T_2^*$ image relative to said reference magnetic resonance $T_2^*$ image, and correcting said second magnetic resonance $T_2^*$ image using the scale and rotation correction values to produce a scale/rotation-corrected second magnetic resonance $T_2^*$ image, position correction means for calculating a cross-correlation between the reference magnetic resonance $T_2^*$ image and the scale/rotation-corrected second magnetic resonance $T_2^*$ image, calculating a position correction value for the scale/rotation-corrected second magnetic resonance $T_2^*$ image comprising a position deviation value of the scale/rotation-corrected second magnetic resonance $T_2^*$ image relative to the reference magnetic resonance $T_2^*$ image, and correcting the scale/rotation-corrected second magnetic resonance $T_2^*$ image using the position correction value to produce a position-corrected second magnetic resonance $T_2^*$ image, and means for displaying the position-corrected second magnetic resonance $T_2^*$ image.

11. A magnetic resonance imaging apparatus according to claim 10, wherein said reference magnetic resonance $T_2^*$ image used by the scale/rotation correction means is a first $T_2^*$ image se among a series of magnetic resonance $T_2^*$ images obtained by said image-forming means.

12. A magnetic resonance imaging apparatus according to claim 10, wherein said reference magnetic resonance $T_2^*$ image used by the scale/rotation correction means is a $T_2^*$ image selected via a console terminal by an operator from among a series of magnetic resonance $T_2^*$ images obtained by said image-forming means.

13. A magnetic resonance imaging apparatus according to claim 10, further comprising:

a stimulus device for giving stimuli to said body to be tested.

14. A magnetic resonance imaging apparatus according to claim 13, wherein said second magnetic resonance $T_2^*$ image used by the scale/rotation correction means is a $T_2^*$ image obtained while stimuli are given to said body to be tested.

* * * * *